(12) United States Patent
Vezzu

(10) Patent No.: US 9,320,534 B2
(45) Date of Patent: Apr. 26, 2016

(54) FINE MEMBRANE FORCEPS WITH INTEGRAL SCRAPING FEATURE

(71) Applicant: Alcon Research, Ltd., Fort Worth, TX (US)

(72) Inventor: Guido Vezzu, Pfungen (CH)

(73) Assignee: Alcon Research, Ltd., Fort Worth, TX (US)

( * ) Notice: Subject to any disclaimer, the term of this patent is extended or adjusted under 35 U.S.C. 154(b) by 50 days.

(21) Appl. No.: 13/713,782

(22) Filed: Dec. 13, 2012

(65) Prior Publication Data

US 2014/0172010 A1    Jun. 19, 2014

(51) Int. Cl.
| | |
|---|---|
| *A61B 17/29* | (2006.01) |
| *A61F 9/007* | (2006.01) |
| *A61B 17/00* | (2006.01) |
| *A61B 17/30* | (2006.01) |
| *A61B 17/32* | (2006.01) |

(52) U.S. Cl.
CPC .............. *A61B 17/29* (2013.01); *A61F 9/00736* (2013.01); *A61B 2017/00353* (2013.01); *A61B 2017/305* (2013.01); *A61B 2017/320004* (2013.01); *A61B 2017/320008* (2013.01)

(58) Field of Classification Search
CPC .................. A61B 17/29; A61B 10/06; A61B 2017/2927; A61B 2017/2945; A61B 2017/2926; A61B 2017/00353; A61B 2017/305; A61B 2017/320008; A61B 2017/320004; A61B 18/1445; A61B 18/1442; A61B 17/282; A61F 9/00736
USPC ............. 606/205–209, 51, 52, 148, 139, 174, 606/170, 191, 46, 158, 151, 167, 185, 108, 606/113, 190, 110, 40, 159, 114, 142, 210, 606/211, 161; 30/131, 124; 403/91; 604/264, 164.01, 521; 600/104, 145, 600/158, 153, 235
See application file for complete search history.

(56) References Cited

U.S. PATENT DOCUMENTS

| | | | |
|---|---|---|---|
| 4,994,079 A | | 2/1991 | Genese et al. |
| 5,078,716 A | | 1/1992 | Doll |
| 5,222,973 A | * | 6/1993 | Sharpe et al. ................. 606/206 |
| 5,234,458 A | | 8/1993 | Metais |
| 5,496,330 A | | 3/1996 | Bates et al. |
| 5,601,572 A | | 2/1997 | Middleman et al. |
| 5,792,145 A | | 8/1998 | Bates et al. |
| 5,855,586 A | | 1/1999 | Habara et al. |
| 5,921,998 A | | 7/1999 | Tano et al. |

(Continued)

FOREIGN PATENT DOCUMENTS

| | | |
|---|---|---|
| WO | 2009067649 A2 | 5/2009 |
| WO | 2011097578 A1 | 8/2011 |
| WO | 2014092956 A1 | 6/2014 |

OTHER PUBLICATIONS

"Grieshaber Revolution DSP", Alcon, Vitreoretinal Product Catalog , 6 pgs., 2012 Novartis 7/12 VIT12052MSA.

(Continued)

*Primary Examiner* — Jocelin Tanner

(57) ABSTRACT

Membrane forceps for performing an ILM or ERM peel procedure include a handle, a tube extending from the handle, and forceps jaws extending from the tube. The forceps jaws may be configured to grasp an ILM or ERM, and may include an outer surface having a roughened surface. The roughened surface may be structurally configured to aid in gaining an edge of the ILM or ERM.

11 Claims, 7 Drawing Sheets

(56) References Cited

U.S. PATENT DOCUMENTS

| | | | |
|---|---|---|---|
| 5,972,021 A * | 10/1999 | Huttner et al. | 606/210 |
| 6,077,274 A | 6/2000 | Ouchi et al. | |
| 6,267,759 B1 | 7/2001 | Quick | |
| 6,340,354 B1 * | 1/2002 | Rambin | 604/22 |
| D456,077 S | 4/2002 | Etter et al. | |
| 6,464,629 B1 | 10/2002 | Boone et al. | |
| 6,575,989 B1 | 6/2003 | Scheller et al. | |
| 6,685,725 B2 | 2/2004 | Attinger et al. | |
| 6,730,076 B2 * | 5/2004 | Hickingbotham | 606/16 |
| 2002/0068954 A1 | 6/2002 | Foster | |
| 2004/0193214 A1 * | 9/2004 | Scheller et al. | 606/205 |
| 2004/0260337 A1 * | 12/2004 | Freed | 606/205 |
| 2008/0183199 A1 | 7/2008 | Attinger | |
| 2011/0015669 A1 | 1/2011 | Corcosteugi | |
| 2014/0135820 A1 | 5/2014 | Schaller et al. | |
| 2014/0379024 A1 | 12/2014 | Schaller et al. | |

OTHER PUBLICATIONS

Prosecution History, U.S. Appl. No. 14/550,470, 42 pages, as of Jan. 6, 2015.
International Searching Authority, International Search Report, PCT/US2013/071055, Feb. 4, 2014, 2 pages.
International Searching Authority, Written Opinion of the International Searching Authority, PCT/US2013/071055, Feb. 4, 2014, 6 pages.

* cited by examiner

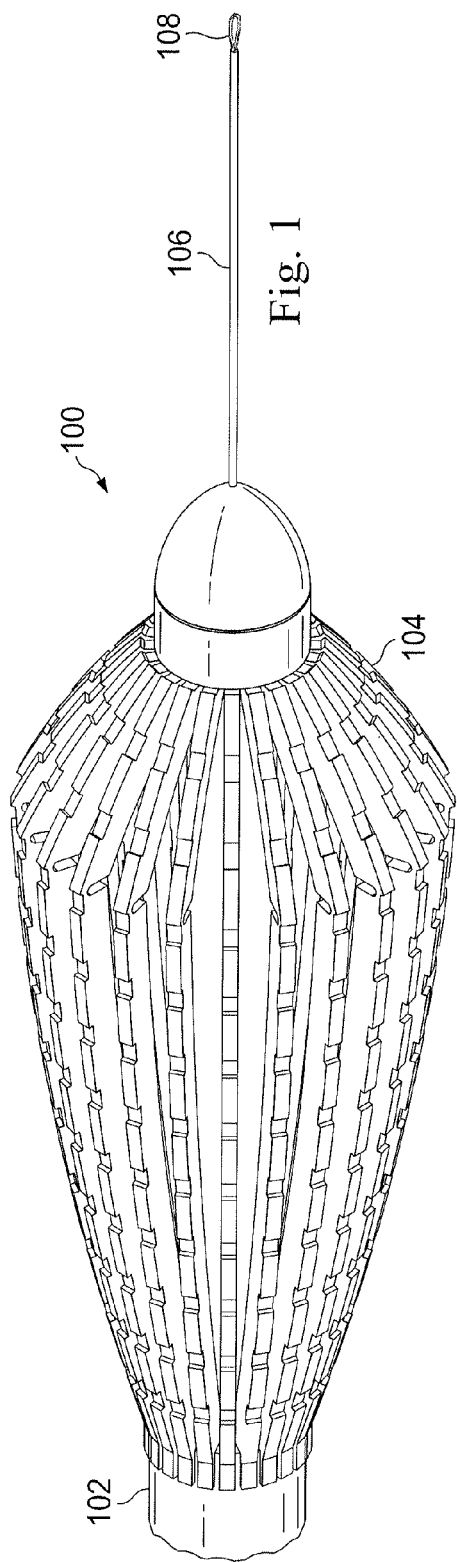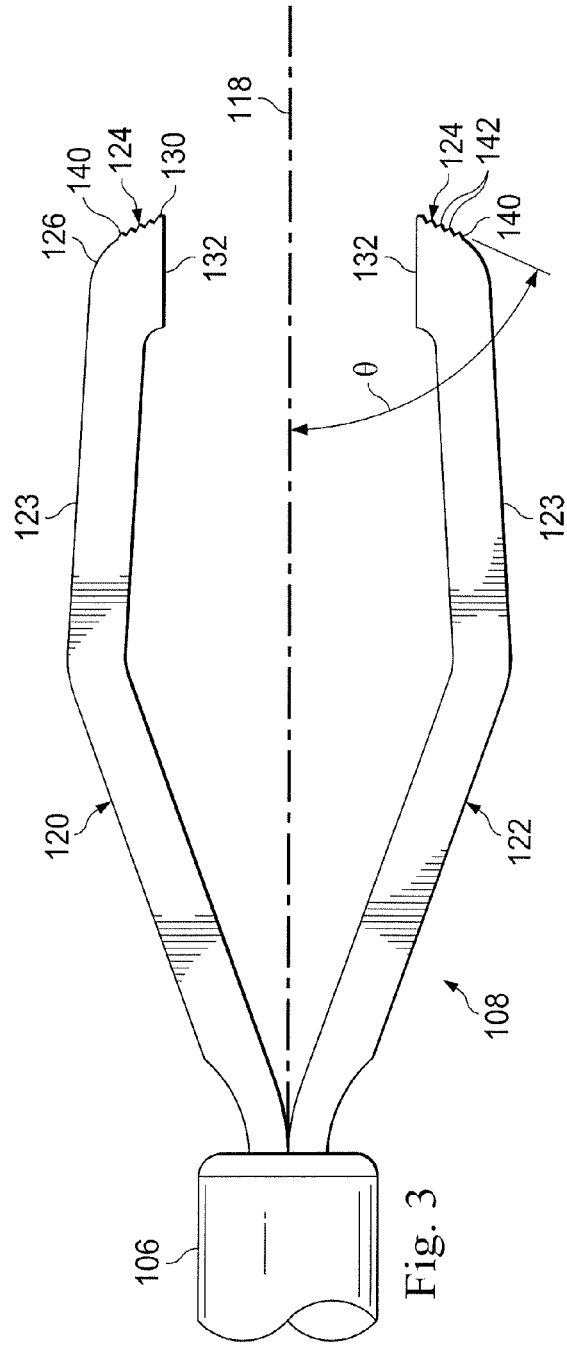

FINE MEMBRANE FORCEPS WITH INTEGRAL SCRAPING FEATURE

BACKGROUND

The devices, systems, and methods disclosed herein relate generally to surgical instruments and techniques, and more particularly, to surgical instruments and techniques for treating an ocular condition.

Internal limiting membrane (ILM) removal and epi-retinal membrane (ERM) removal are useful surgical treatments of different macular surface diseases. However, the surgical techniques for ILM and ERM peeling require skill and patience. Precise and carefully constructed surgical instruments are used for each segment of the surgical technique.

The surgical treatment itself includes grasping an edge of the membrane, and peeling the membrane. The surgical technique itself is a two-step procedure. First, the surgeon must gain an edge of the membrane. Some surgeons use a scraper to gain the edge. Next, the surgeon introduces a special forceps to grasp and peel the membrane. However, since each step requires patience and precision, a surgeon may sometimes scrape and then attempt to grasp the tissue multiple times during a single surgical procedure. Each time that a different tool is desired, the surgeon removes the instrument being used from the surgical site, and introduces the desired surgical instrument. This can be time consuming, and often requires the surgeon to make judgment calls as to when an alternative instrument might or might not be needed.

The present disclosure is directed to devices, systems, and methods that address one or more of the disadvantages of the prior art.

SUMMARY

In an exemplary aspect, the present disclosure is directed to membrane forceps for performing an ILM or ERM peel procedure. The membrane forceps include a handle, a tube extending from the handle, and forceps jaws extending from the tube. The forceps jaws may be configured to grasp an ILM or ERM, and may include an outer surface having a roughened surface. The roughened surface may be structurally configured to aid in gaining an edge of the ILM or ERM.

In one aspect, the forceps jaws may include a first jaw and a second jaw, with the first jaw comprising a leading edge extending obliquely relative to a longitudinal axis extending between the first and second jaws. In one aspect, the roughened surface comprises a series of ridges. The series of ridges may be disposed substantially parallel to the leading edge.

In another aspect, the roughened surface may include surface features having a peak to valley height within a range of about 3-40 microns. In yet another aspect, the roughened surface comprises an array of points extending away from the outer surface.

In another aspect, the outer surface is angled relative to a longitudinal axis to lie substantially parallel to tissue within the eye that is to be scraped when the instrument is in the eye. The outer surface may be angled relative to the longitudinal axis at an angle having a value between about 25 degrees and 65 degrees. In one aspect, the forceps jaws comprise a first jaw and a second jaw, each of the first and second jaws comprising a leg and a bend that is made in an oblique direction relative to a longitudinal axis extending between the first and second jaws.

In another exemplary aspect, the present disclosure is directed to a surgical instrument for performing an ILM or ERM peel procedure that may include a handle, a tube extending from the handle, and forceps jaws extending from the tube. The forceps jaws may include a first jaw and a second jaw, with the first and second jaws being asymmetrical and having a leading edge extending obliquely relative to a longitudinal axis through the surgical instrument. Each of the first jaw and the second jaw may include an outer surface having roughening features. The outer surface may extend in a proximal direction from the leading edge. The roughening features may be structurally configured to aid in gaining an edge of the ILM or ERM.

In one aspect, the first jaw and the second jaw each comprise a leg portion and bend between the leg portion and the outer surface portion having the roughening features. In another aspect, the bend in the first jaw and the second jaw is oblique relative to the longitudinal axis. In an aspect, the outer surface is angled relative to the longitudinal axis at an angle having a value between about 25 degrees and 65 degrees. In an aspect, the outer surface comprises surface features having a peak to valley height within a range of about 3-40 microns.

In yet another exemplary aspect, the present disclosure is directed to a surgical method comprising introducing membrane forceps into a globe of a patient's eye for the purpose of performing an ILM or ERM peel procedure. The membrane forceps may include an outer surface having a roughened portion structurally configured to aid in gaining an edge of the ILM or ERM. The method also may include scraping the ILM or ERM with the roughened surface to gain an edge, and without removing the membrane forceps, grasping a portion of the ILM or ERM between two jaws with the surgical instrument.

In one aspect, scraping the ILM or ERM comprises engaging the ILM or ERM with ridges forming the roughened portion of the outer surface. In another aspect, the ridges forming the roughened portion of the outer surface are disposed in lines substantially parallel with a leading edge of the surgical instrument. In yet another aspect, the roughened portion is a flat portion, and the method includes orienting the flat portion so that it is substantially parallel to the membrane or order to scrape the ILM or ERM with the roughened portion. In another aspect, grasping a portion of the ILM or ERM comprises squeezing a handle portion to bring the two jaws together. In another aspect, grasping a portion of the ILM or ERM comprises gripping at least a portion of the membrane between grip faces on each of the two jaws.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings illustrate embodiments of the devices and methods disclosed herein and together with the description, serve to explain the principles of the present disclosure.

FIG. 1 illustrates a perspective view of an exemplary surgical instrument according to one embodiment consistent with the principles of the present disclosure.

FIG. 3 illustrates a side view showing surface features on the distal portion of the exemplary surgical instrument according to an embodiment consistent with the principles of the present disclosure.

DETAILED DESCRIPTION

Figure 2:
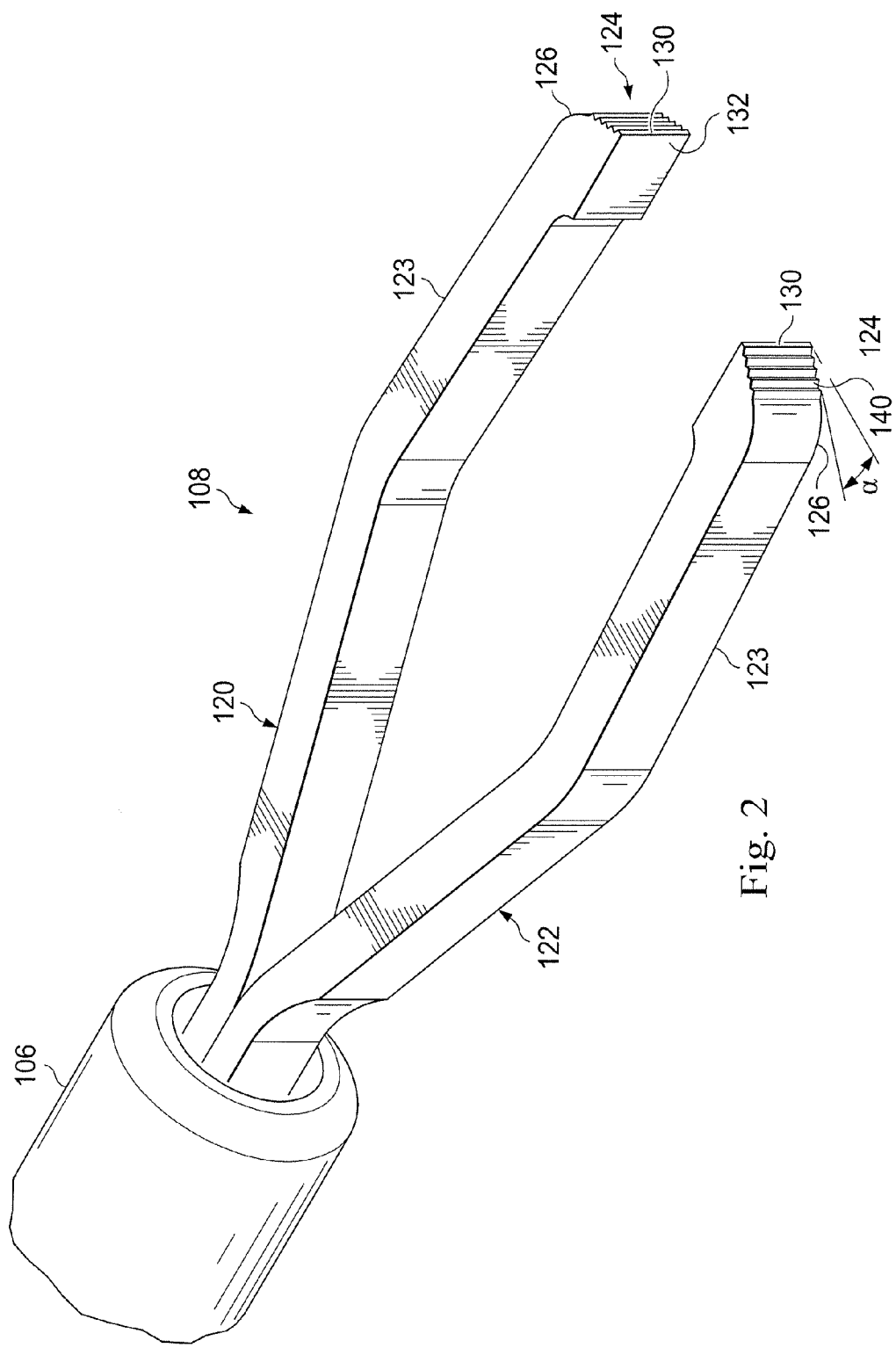
FIG. 2 illustrates a perspective view of a distal portion of the exemplary surgical instrument according to an embodiment consistent with the principles of the present disclosure.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately. For simplicity, in some instances the same reference numbers are used throughout the drawings to refer to the same or like parts.

The present disclosure relates generally to devices, systems, and methods for ILM and ERM peeling and removal. These types of procedures require precision and can be difficult to perform for an unpracticed surgeon. Because the procedure takes place inside the globe of the eye, the surgeon must take great care to avoid any lasting trauma or tissue damage. Introducing and removing instruments from the eye itself takes time. In addition, because of convenience, some surgeons may be inclined to utilize the instrument within the eyes rather than removing and introducing a different, perhaps more effective, instrument to accomplish desired objectives.

The devices, systems, and methods disclosed herein include a forceps designed with a scraper feature to increase the efficiency of the surgical procedure, potentially resulting in a better patient outcome. More particularly, the area on the jaws forming a forceps is roughened in a way that enables a user to safely rupture the ILM or ERM using a scraping motion so that an edge of the membrane can be more easily grasped by the forceps. In the embodiments disclosed herein, the forceps feature still remains independent of the scraper feature. That is, the forceps and the scraper features do not impact the successful utilization of each other. In some embodiments, the scraper area on the forceps is disposed to be fully exploited for all scraper needs. Accordingly in use, the surgeon may no longer need to determine a threshold for the insertion of a scraper to maintain a difficult peeling of an adherent membrane. That is, whenever scraping would be opportune, the feature is already there. This may increase the efficiency of the initiation, performance, and maintenance of the peeling procedure.

FIG. 1 illustrates a surgical instrument 100 shown as membrane forceps having a handle 102, a probe actuation handle 104, a probe actuation tube 106, and a probe tip shown as forceps jaws 108. The handle 102 may be made of any suitable material, and may be formed by any method, such as for example, injection molding or machining. It may be made of a thermoplastic or metal and may be textured or knurled to improve gripping. The actuation handle 104 may be made from any suitable springy material having a memory, such as titanium, stainless steel or suitable thermoplastic. The tube 106 may be any suitable medical grade tubing, such as titanium, stainless steel, or suitable polymer and is sized so that the forceps jaws 108 reciprocate easily within. The forceps jaws 108 are generally made from stainless steel or titanium, but other materials may also be used.

The surgical instrument 100 is designed so that in use, when the actuation handle 104 is in its relaxed stated, the forceps jaws 108 protrude a relatively large distance from the tube 106. Squeezing actuation handle 104 forces the front portion of the actuation handle 104 forward relative to the handle 102. The forward movement of the front portion of the actuation handle 104 is transferred to the tube 106, causing the tube 106 to slide forward over a distal portion of the forceps jaws 108, thereby compressing together the jaws 108. The amount of movement of tube 106 over the forceps jaws 108 can be controlled easily by varying the outer diameter of the actuation handle 104 in its relaxed stated.

FIGS. 2 and 3 show the forceps jaws 108 in greater detail. The forceps jaws 108 include two jaws, referred to herein as a jaw 120 and a jaw 122 extending from a distal end of the actuation tube 106. As shown in FIG. 2, the two jaws 120, 122 extend along a longitudinal axis 118 that may be defined by the tube 106.

Each of the jaws 120, 122 includes a projecting leg 123 and a distal gripping tip 124. The legs 123 extend from the actuation tube 106. A bend 126 in the outer surface of the legs forms an intersection of the leg 123 and a leading side of the gripping tip 124.

The gripping tips 124 each include a leading edge 130 at the distal ends and a grip face 132. In the embodiment disclosed, the leading edge 130 of each jaw 120, 122 lies in a plane substantially perpendicular to the longitudinal axis 118.

The grip faces 132 of the two jaws 120, 122 are configured to abut each other when the forceps jaws 108 are closed, and may be used to grip tissue therebetween. In this example the grip faces 132 are formed to lie in substantially parallel planes when the forceps jaws 108 are in a closed or clamped position.

The gripping tips 124 also include a gripping tip distal surface 140 that opposes the grip face 132. In this example, the gripping tip distal surface 140 is angled relative to the longitudinal axis at an angle θ. The angle θ may be an angle taken along a plane through the longitudinal axis 118 and an angle θ having a value between about 25 degrees and 65 degrees. In other embodiments, the angle θ is between about 35 and 65 degrees. In yet another embodiment, the angle θ is formed between about 45 and 65 degrees relative to the longitudinal axis. In addition, in some examples, the gripping tip distal surface 140 is formed as a substantially flat surface. In one example, the distance between the leading edge 130 and the bend 126 is within a range of about 0.1 mm-0.5 mm, and the width across the gripping tip distal surface is with a range of about 0.2 mm-0.9 mm. The jaws 120, 122 may be sized to fit within the tube 106 when the tube 106 is 20 gauge tube, a 23 gauge tube, a 25 gauge tube, or a 27 gauge tube. Other sizes are contemplated.

The gripping tip distal surface 140 includes roughening features 142 that enable gaining the membrane by scraping the membrane in order to rupture it so that an edge of the membrane may be grasped and peeled. In this example, the roughening features 142 are manually formed using a file drawn across the gripping tip distal surface 140 of the forceps to roughen the surface. In some examples, the roughening features are formed in a series of lines or grooves formed when the file is drawn in a lateral direction relative to the longitudinal axis, thereby creating a direction of grain extending in the lateral direction relative to the longitudinal axis. Accordingly, these grooves or features may extend in a direction substantially parallel to the leading edge 130. In this example, substantially parallel is intended to mean having a deviation of about ten degrees or less from parallel. In other examples, the roughening features are formed by drawing the file in the longitudinal direction along the gripping tip distal surface 140, forming a grain extending substantially in the longitudinal direction. Substantially in the longitudinal direction is intended to mean having a deviation of about ten degrees or less from the direction of the longitudinal axis. Other embodiments have the grain of the roughening features formed in other oblique directions.

In some examples, the roughening features are formed on the gripping tip distal surface 140 using a laser cutter. A laser cutter may be used to form roughening features 142 having a specific direction. In one embodiment, the roughening features 142 include a series of ridges. These may include a particular shape, such as a saw-tooth shape for example. Other embodiments include knurled roughening features. Some embodiments include roughening features formed as an array of peaks. In some embodiments, these peaks each have a point, as may occur in diamond-shaped knurls. Other roughening features are contemplated. Depending on the embodiment, the roughening surface 140 may include features 142 having a peak to valley height within a range of about 3-40 microns. In some embodiments, the peak to valley height is within a range of about 3-20 microns, while in other embodiments, the peak to valley height is within a range of about 5-10 microns.

In some embodiments, the ridges are formed in rows as in the example shown in FIGS. 2 and 3. Any of the roughening features may be formed in rows and, depending on the embodiment, may be substantially parallel to the leading edge 130 of the jaws 120, 122. In one example, the surface roughening features 142 extend onto and form a part of the leading edge. The roughening features 142 may be formed using any of a plurality of methods including filing, grinding, scraping, machining, blasting, rolling, etching, and laser cutting, among others. While shown with the roughening features 142 on the outer surface 140, some embodiments include roughening features on the edges and sides of the gripping tip 124.

Figure 4:
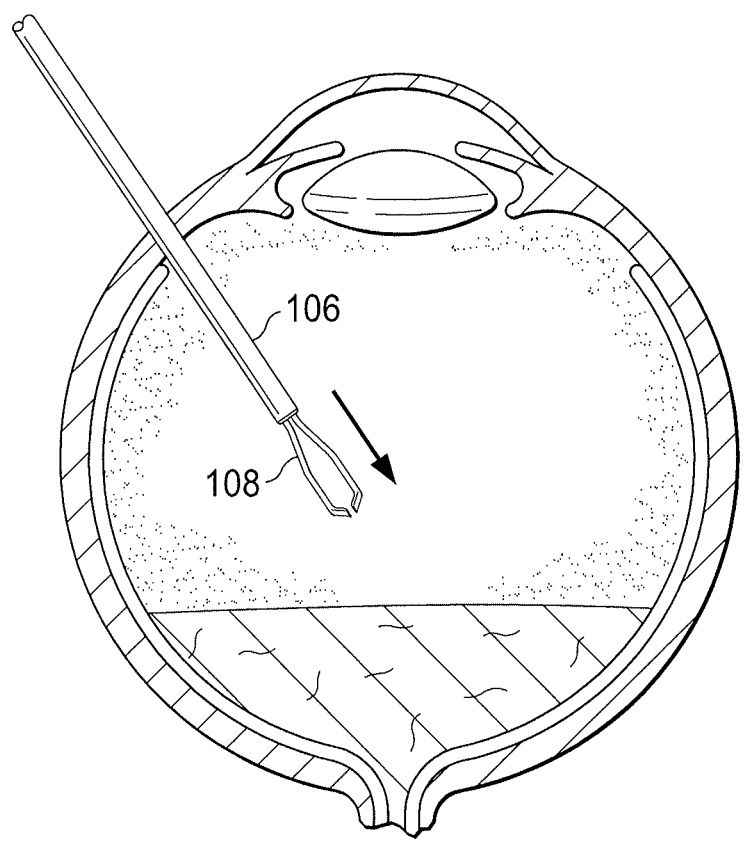
FIG. 4 illustrates a portion of the exemplary surgical instrument of FIG. 1 disposed within an eye of a patient during a surgical procedure according to an embodiment consistent with the principles of the present disclosure.
Figure 5:
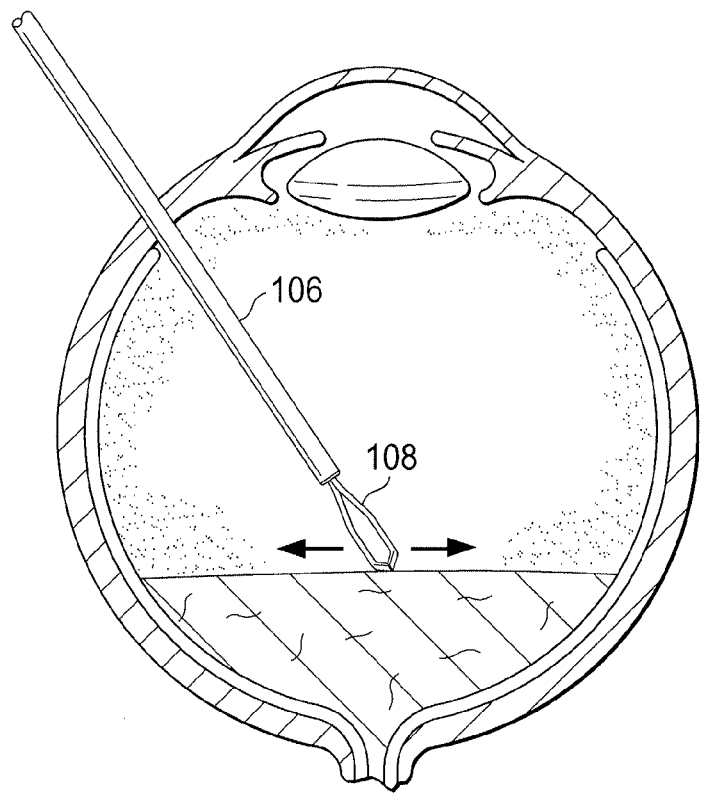
FIG. 5 illustrates a portion of the exemplary surgical instrument of FIG. 1 disposed within an eye of a patient during a surgical procedure according to an embodiment consistent with the principles of the present disclosure.
Figure 6:
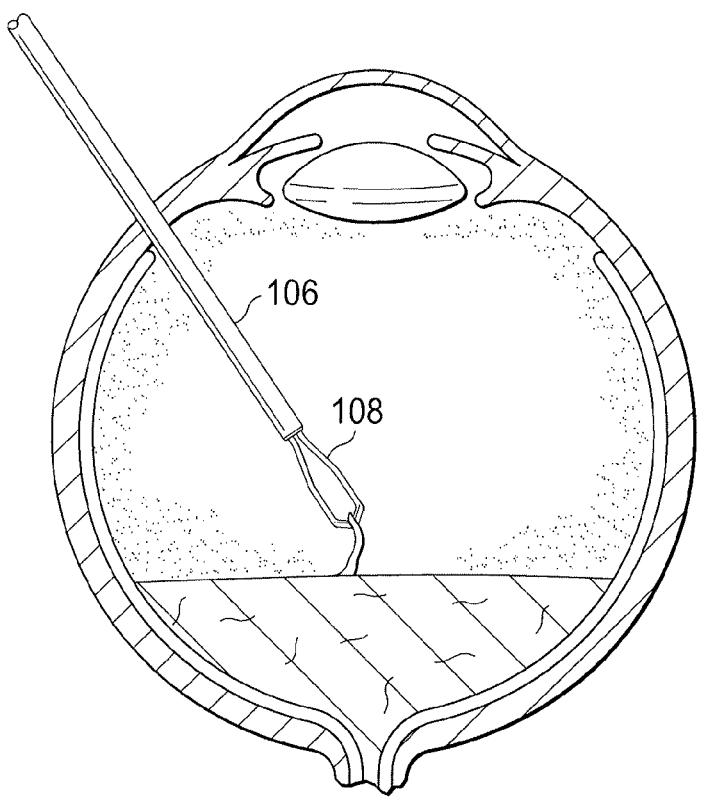
FIG. 6 illustrates a portion of the exemplary surgical instrument of FIG. 1 disposed within an eye of a patient during a surgical procedure according to an embodiment consistent with the principles of the present disclosure.

FIGS. 4-6 show an exemplary technique of using the surgical instrument in an ILM or ERM peeling procedure. For purposes of this disclosure, the technique will not describe cutting and removing the vitreous and posterior hyaloid membrane.

During the procedure, the surgical instrument 100 is introduced into the vitreous through an incision in the sclera, as shown in FIG. 4. The instrument 100 is advanced through the vitreous toward the macula. Some techniques include introducing the distal tip with the jaws 120, 122 in a closed or compressed condition into the globe and through the fluid within the globe (this may be vitreous or may be, for example, a saline solution introduced during removal of the vitreous). Other techniques include introducing the distal tip with the jaws 120, 122 in an open condition through the vitreous, and then closing jaws prior to engaging the ILM or ERM. Additional instruments such as a light pipe, also may be introduced in order to provide visualization to the surgeon.

Peeling the ILM or ERM is a two-phase process. The first phase of the procedure is to gain an edge of the ILM or ERM. The second phase is to grasp and peel the membrane.

The first phase of the procedure may include placing the surgical instrument gripping tip distal surface 140 in contact with the ILM or ERM as shown in FIG. 5. As indicated above, the jaws are placed in a closed condition prior to containing the ILM or ERM. The angle θ of the gripping tip distal surface 140 is formed so that the gripping tip distal surface 140 lies substantially parallel to the surface of the membrane. Accordingly, the gripping tip distal surface 140 may lie relatively flat on the membrane. In some aspects, the instrument itself may extend at an angle, such as, for example only, about 60 degrees from the membrane surface. At this angle, in some examples, the angled roughened scraping surface 140 may be formed to lie substantially flat against the membrane.

With the jaws in the closed condition, slight side-to-side or back-and-forth movement may be used to scrape the ILM or ERM with the roughening features 142 to gain an edge by rupturing the membrane, thereby creating an edge of the membrane that can be grasped. Some techniques include moving the jaws back and forth in a direction transverse to the grain of the surface roughening features 142. This may permit the surface roughening features to act against the membrane and result in easier membrane rupturing. After the surgeon creates an edge by rupturing the membrane with the roughened scraping surface 140 on the surgical instrument 100, the surgeon may then proceed to phase two of the surgical procedure.

Because of its structural arrangement, grasping and peeling the membrane can be accomplished without removing the surgical instrument 100 from the globe of the eye. Instead, the surgeon is able to grasp and peel the membrane with the same surgical instrument used to scrape the membrane and gain an edge. Using the same surgical instrument 100, after gaining the edge of the membrane, the surgeon may immediately use the two jaws to begin to grasp the membrane edge gained during the scraping procedure as shown in FIG. 6. In order to grasp the tissue between the grip faces 132, the surgeon may rotate the forceps 90 degrees so that the grip faces are substantially perpendicular to the macula. This may permit the surgeon to more easily grasp the membrane between the jaws. If necessary, the surgeon may attempt to grasp the membrane between the leading tips 136 when very fine or minute segments of the tissue are available.

Advantageously, if the surgeon is unable to grasp the membrane with the instrument 100, or if the membrane tears and the surgeon need to gain another edge of the membrane, the surgeon may be able to use the roughening features 142 on the instrument 100 again, without removing the instrument 100 from the patient. Accordingly, the surgeon does not need to make a conscious determination whether to withdraw the forceps and insert a scraper to maintain a difficult peeling of an adherent membrane. Instead, the scraping or roughening structure may be used anytime desired. This may ease and simplify the initiation, performance, and maintenance of the peeling procedure.

Figure 7:
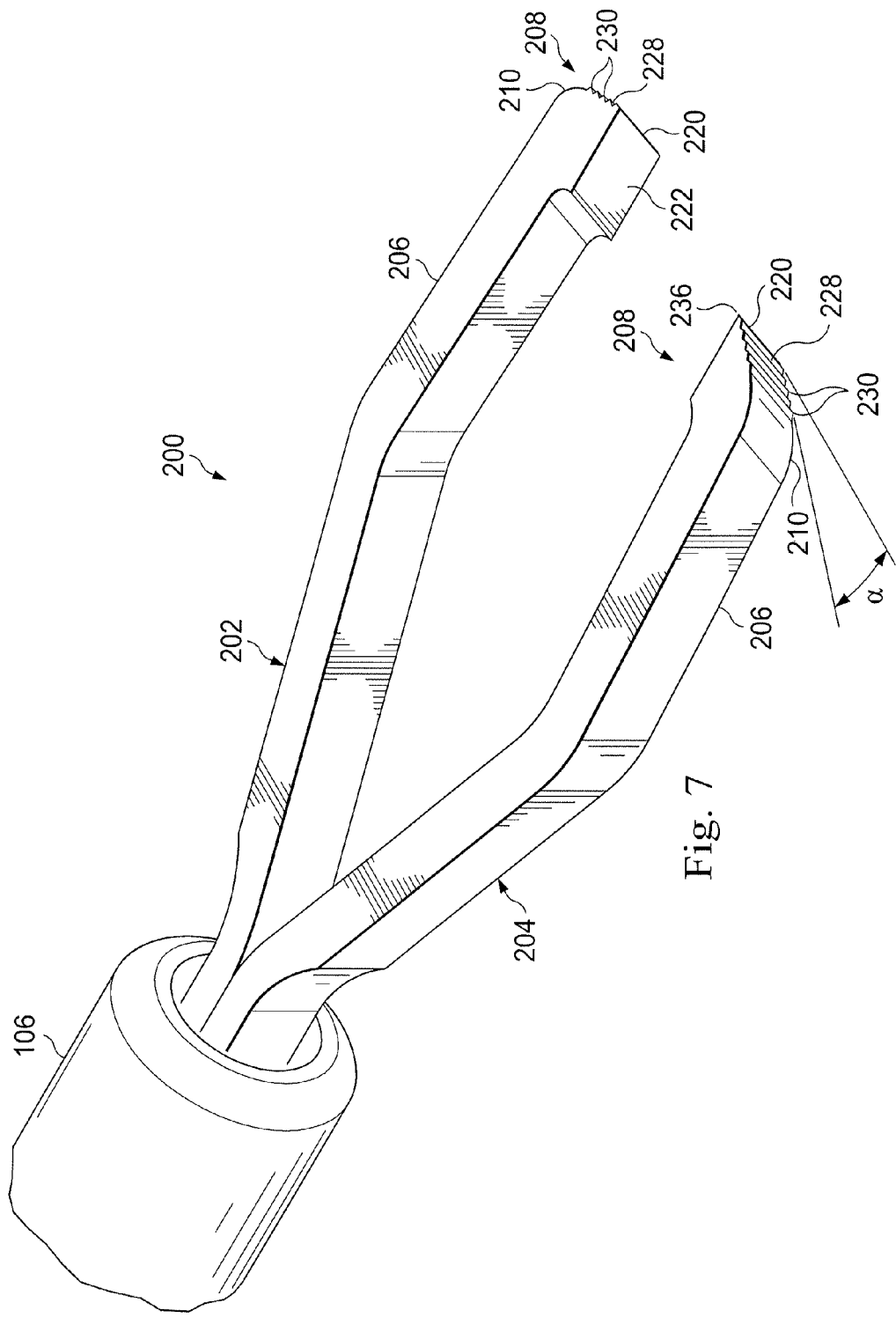
FIG. 7 illustrates a perspective view of a distal portion of an exemplary surgical instrument according to an embodiment consistent with the principles of the present disclosure.
Figure 8:
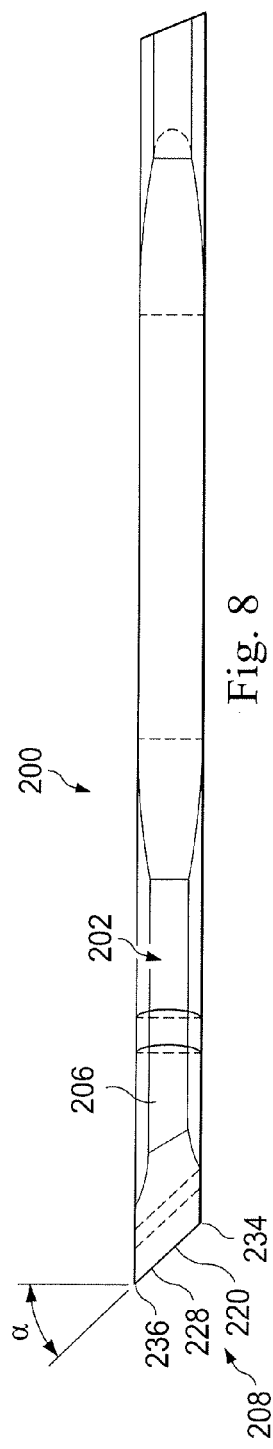
FIG. 8 illustrates a top view showing surface features on the distal portion of the exemplary surgical instrument of FIG. 7 according to an embodiment consistent with the principles of the present disclosure.

FIG. 7 shows a portion of another embodiment of forceps jaws referenced herein by the numeral 200. FIG. 8 shows a top view of the forceps jaws 200. This embodiment includes jaws formed so that the surgeon may perform the scraping step and then grasp the membrane without rotating the forceps. This will be explained further below.

The forceps jaws 200 include jaws 202 and 204, with each having a projecting leg 206 and a distal gripping tip 208. The legs 206 extend from the actuation tube 106 of a surgical instrument, such as the surgical instrument 100 in FIG. 1. A bend 210 in the outer surface of the legs forms an intersection of the leg 206 and an opposing side of the gripping tip 208. In this embodiment, the gripping tips 208 angle toward each other and include an asymmetrical arrangement. Accordingly, while the jaws 202, 204 mirror each other, the jaws form asymmetric forceps.

The gripping tips 208 each include a leading edge 220 at the distal ends and a grip face 222. In the embodiment disclosed, the leading edge 220 of each jaw 202, 204 lies in a plane oblique to the longitudinal direction or axis. Like the bend 210, the leading edge 220 at the distal end is formed at an oblique angle, defined by the angle α. Accordingly, the leading edge 220 angles from a trailing tip 234 to a leading tip 236. This angled edge permits the leading edge 220 to lie parallel to a surface, such a tissue surface, even while the surgical instrument 100 is held at an oblique angle relative to the tissue surface. In addition, because of the arrangement, a surgeon may use any part of the entire leading edge 220 to grasp tissue since the whole leading edge may be parallel to the tissue during a procedure. In the embodiment disclosed, the leading edge 130 is angled relative to the longitudinal axis 118 at an angle α having a value between about 35 degrees and 80 degrees. In other embodiments, the angle α is between about 30 and 70 degrees. In yet another embodiment, the angle α is formed between about 30 and 50 degrees. In some embodiments, the bend 210 at the intersection of the leg 206 and the gripping tips 208 is also formed parallel to the leading edge 220 and therefore is also formed at an oblique angle α.

Like the forceps jaws described with reference to FIGS. 2 and 3, the grip faces 222 in the forceps jaws 200 are configured to abut each other when the forceps jaws are closed, and may be used to grip tissue therebetween. In this example the grip faces 222 are formed to lie in substantially parallel planes when the forceps jaws 108 are in a closed or clamped position.

The gripping tips 208 also include a gripping tip distal surface 228 that opposes the grip face 222. In this example, the gripping tip distal surface 228 is formed to have at least a portion that is angled perpendicular to the longitudinal direction so that when the grip faces 222 are pressed together, the gripping tip distal surface 228 forms a leading plane as represented in FIG. 8. As such, in some examples, the gripping tip distal surface 228 is formed as a substantially flat surface. The jaws 120, 122 may be sized to fit within the tube 106 when the tube 106 is 20 gauge tube, a 23 gauge tube, a 25 gauge tube, or a 27 gauge tube. Other sizes are contemplated.

The gripping tip distal surface 228 includes roughening features 230 that enable gaining the membrane by scraping the membrane in order to rupture it so that an edge of the membrane may be grasped and peeled. In this example, the roughening features 230 are manually formed using a file drawn across the gripping tip distal surface 228 of the forceps to roughen the surface. The roughening features may be formed or shaped as discussed above, and in some embodiments, are substantially parallel to the leading edge 220.

Figure 9:
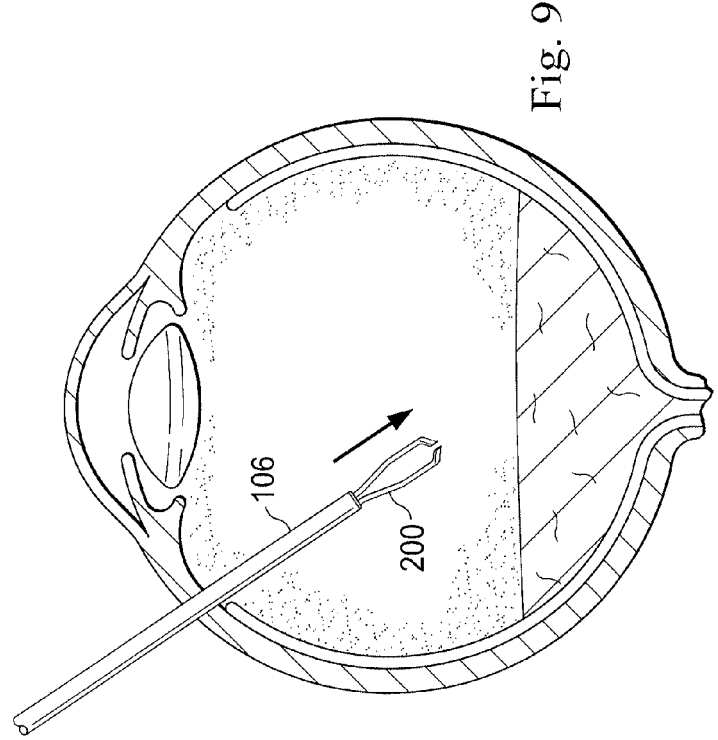
FIG. 9 illustrates a portion of the exemplary surgical instrument of FIG. 7 disposed within an eye of a patient during a surgical procedure according to an embodiment consistent with the principles of the present disclosure.
Figure 10:
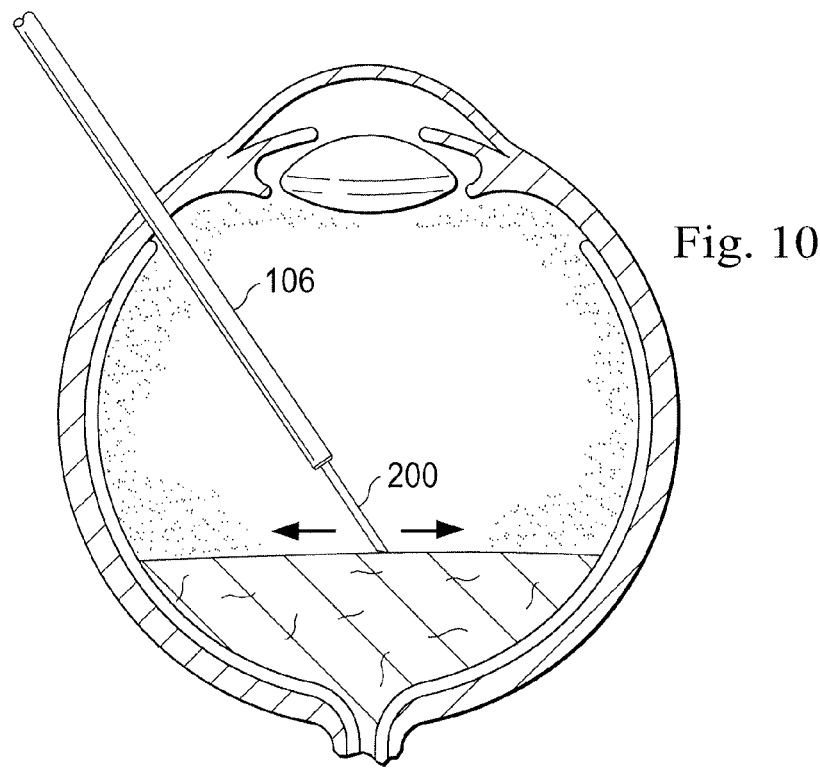
FIG. 10 illustrates a portion of the exemplary surgical instrument of FIG. 7 disposed within an eye of a patient during a surgical procedure according to an embodiment consistent with the principles of the present disclosure.
Figure 11:
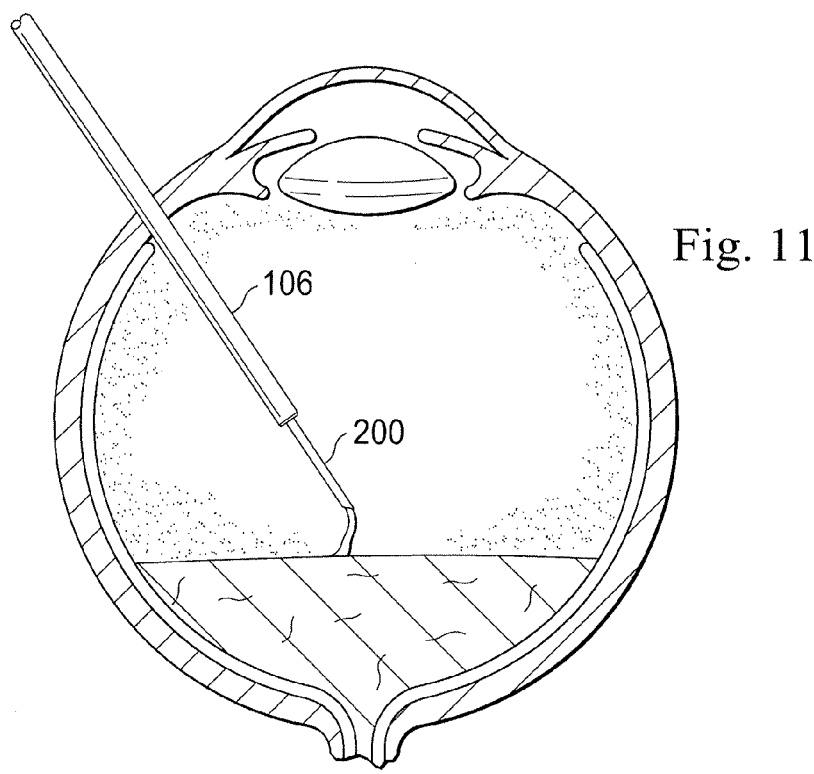
FIG. 11 illustrates a portion of the exemplary surgical instrument of FIG. 7 disposed within an eye of a patient during a surgical procedure according to an embodiment consistent with the principles of the present disclosure.

FIGS. 9-11 show an exemplary technique of using the surgical instrument in an ILM or ERM peeling procedure. Only the differences from the technique above will be described in detail, as much of the description above applies to the technique using the forceps 200.

Referring to FIG. 9, the instrument is introduced into the globe of the eye. In FIG. 10, the forceps jaws 200 are placed against the membrane. Here, because the leading edge is formed at the angle α, and because the gripping tip distal surface 228 is formed to be a flat leading surface, the gripping tip distal surface 228 lies in a plane substantially parallel to the membrane. In one embodiment, the surgeon may then scrape the membrane using the gripping tip distal surface 228 on both of the jaws at the same time.

In FIG. 10, the forceps are shown from the side angle. Because the leading edge is angled, and the gripping tip distal surface 228 is angled, the scraping may occurs while the forceps jaws are already positioned for grasping scraped tissue. FIG. 11 shows the forceps jaws gripping a membrane tissue. The grasping of the membrane occurs without rotating the instrument 90 degrees. That is, during the scraping step in FIG. 10, the leading edge of each jaw is already abutting against the membrane in the closed position. The surgeon need only open the membrane and close it to grasp the scraped tissue.

Because the ILM or ERM peel procedure may potentially be performed without removing and introducing separate instruments into the eye to rupture or scrape the membrane and to grasp the membrane, fewer instruments may be used in the surgical procedure. This may increase efficiency of the procedure, may result in less opportunity for error, and may provide better patient outcome.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure

I claim:
1. Membrane forceps for performing an ILM (internal limiting membrane) or ERM (epiretinal membrane) peel procedure; comprising:
 a handle;
 a tube extending from the handle; and
 forceps jaws extending from the tube, the forceps jaws being configured to grasp an ILM or ERM between two opposing grip faces configured to abut each other when the forceps jaws are closed, the forceps jaws also comprising an outer surface, external to the grip faces, having a series of ridges, the series of ridges being structur- ally configured to aid in scraping the ILM or ERM and gaining an edge of the ILM or ERM;

wherein the series of ridges comprise surface features having a peak to valley height within a range of about 3-40 microns;

wherein the outer surface is angled relative to a longitudinal axis of the tube at an angle having a value between about 25 degrees and 65 degrees to lie substantially parallel to tissue within an eye that is to be scraped when the membrane forceps is in the eye;

wherein the series of ridges are substantially parallel to each other; and wherein the series of ridges are disposed substantially parallel to leading edges at distal-most ends of the forceps jaws, wherein the leading edges lie in a plane substantially perpendicular to the longitudinal axis of the tube.

2. The membrane forceps of claim 1, wherein the forceps jaws comprise a first jaw and a second jaw, the first jaw comprising a leading edge, of the leading edges, extending obliquely relative to the longitudinal axis of the tube extending between the first and second jaws.

3. The membrane forceps of claim 1, wherein the series of ridges comprise an array of points extending away from the outer surface.

4. The membrane forceps of claim 1, wherein the forceps jaws comprise a first jaw and a second jaw, each of the first and second jaws comprising a leg and a bend that is made in an oblique direction relative to the longitudinal axis of the tube extending between the first and second jaws.

5. The membrane forceps of claim 1, wherein the forceps jaws are configured to be closed by forward motion of the tube over legs of the forceps jaws.

6. The membrane forceps of claim 1, wherein at least one of the series of ridges forms a distal most line of the forceps opposite the handle.

7. A surgical instrument for performing an ILM (internal limiting membrane) or ERM (epiretinal membrane) peel procedure; comprising:
   a handle;
   a tube extending from the handle; and
   forceps jaws extending from the tube, the forceps jaws comprising a first jaw and a second jaw, the first and second jaws being asymmetrical and having a leading edge, at a distal-most end of the jaw, extending obliquely relative to a longitudinal axis through the surgical instrument, each of the first jaw and the second jaw comprising a respective grip face, wherein the respective grip faces are configured to abut each other when the forceps jaws are closed, and wherein the first and second jaw further comprise an outer surface, external to the grip faces, having a series of ridges, the outer surface extending in a proximal direction from the leading edge, the series of ridges being structurally configured to aid in gaining an edge of the ILM or ERM;

wherein the series of ridges comprise surface features having a peak to valley height within a range of about 3-40 microns;

wherein the outer surface is angled relative to a longitudinal axis of the surgical instrument at an angle having a value between about 25 degrees and 65 degrees to lie substantially parallel to tissue within an eye that is to be scraped when the instrument is in the eye;

wherein the series of ridges are substantially parallel to each other; and wherein the series of ridges are disposed substantially parallel to the leading edges, wherein the leading edges lie in a plane substantially perpendicular to the longitudinal axis of the surgical instrument.

8. The surgical instrument of claim 7, wherein the first jaw and the second jaw each comprise a leg portion and bend between the leg portion and the outer surface having the series of ridges.

9. The surgical instrument of claim 8, wherein the bend in the first jaw and the second jaw is oblique relative to the longitudinal axis.

10. The membrane forceps of claim 7, wherein the forceps jaws are configured to be closed by forward motion of the tube over legs of the forceps jaws.

11. The membrane forceps of claim 7, wherein at least one of the series of ridges forms a distal most line of the forceps opposite the handle.

* * * * *